United States Patent [19]

Tsuchiya et al.

[11] 4,154,817
[45] May 15, 1979

[54] SMELL-REMOVING AND DEODORIZING COMPOSITION AND PROCESS OF USING SAME

[75] Inventors: Yoshimi Tsuchiya, Yachiyo; Yoshinori Naganuma, Tokyo; Haruhiko Arai, Narashino, all of Japan

[73] Assignee: Kao Soap Co., Ltd., Tokyo, Japan

[21] Appl. No.: 590,029

[22] Filed: Jun. 25, 1975

[30] Foreign Application Priority Data

Jul. 2, 1974 [JP] Japan .................................. 49/75508

[51] Int. Cl.$^2$ ............................................. A61L 13/00
[52] U.S. Cl. .................................... 424/76; 424/316; 424/317
[58] Field of Search ......................... 424/76, 317, 316

[56] References Cited

U.S. PATENT DOCUMENTS

| | | | |
|---|---|---|---|
| 2,562,208 | 7/1951 | Papa et al. ............................ | 424/289 |
| 2,795,554 | 6/1957 | Shumard .............................. | 252/107 |
| 2,998,390 | 8/1961 | Hamilton .............................. | 424/76 |
| 3,509,254 | 4/1970 | Krotinger, Jr. et al. ......... | 424/317 X |
| 3,903,259 | 9/1975 | Hart ..................................... | 424/76 |

OTHER PUBLICATIONS

Scheffold et al., Helv. Chim. Acta., 50, 798–808, (1967).

Papa et al., J. A. Chem. Soc., vol. 70, pp. 3356–3360 (1948).

Kirchner et al., J. A. Chem. Soc., vol. 71, pp. 1210–1213 (1949).

*Primary Examiner*—Allen J. Robinson
*Attorney, Agent, or Firm*—Blanchard, Flynn, Thiel, Boutell & Tanis

[57] ABSTRACT

A smell-removing and deodorizing composition comprising as an effective ingredient a beta-substituted acrylic acid or salt thereof, having the formula:

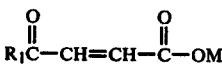

or

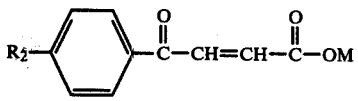

wherein M is hydrogen, alkali metal, alkaline earth metal or ammonium, $R_1$ is alkyl having 1 to 20 carbon atoms or alkenyl having 2 to 20 carbon atoms, and $R_2$ is hydrogen or alkyl having 1 to 20 carbon atoms or alkenyl having 2 to 20 carbon atoms.

4 Claims, No Drawings

SMELL-REMOVING AND DEODORIZING COMPOSITION AND PROCESS OF USING SAME

BACKGROUND OF THE INVENTION

1. Field of the Invention

This invention relates to a smell-removing and deodorizing agent having an excellent effect for removing bad smells generated in lavoratories, dust bins, cattle stalls and the like, especially odors of mercaptans, hydrogen sulfide, ammonia and amines.

2. Description of the Prior Art

Various methods have heretofore been adopted for removing bad smells of mercaptans, hydrogen sulfide, ammonia and the like. Acrylic acid alkyl esters (such as lauryl methacrylate) are used as chemical deodorizing agents in various fields. These deodorizing agents are effective for removing bad smells of lower alkyl amines such as dimethyl amine, but they fail to remove bad smells of mercaptans and hydrogen sulfide.

SUMMARY OF THE INVENTION

It is a primary object of this invention to overcome the defects of conventional deodorizing agents. According to the invention, this object is attained by employing a smell-removing and deodorizing composition comprising as an effective ingredient a beta-substituted acrylic acid or salt thereof having the formula (I) or formula (II):

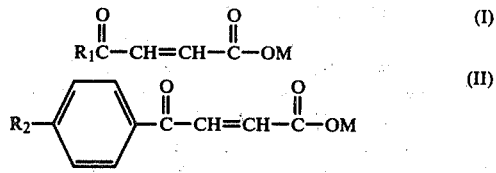

wherein M is hydrogen, alkali metal, alkaline earth metal or ammonium, $R_1$ is alkyl having 1 to 20 carbon atoms or alkenyl having 2 to 20 carbon atoms, and $R_2$ is hydrogen or the same organic groups as mentioned above for $R_1$.

As examples of the organic groups $R_1$ and $R_2$ in the above formulae (I) and (II), there can be mentioned alkyl and alkenyl groups having up to 20 carbon atoms, such as methyl, ethyl propyl, butyl, octyl, 2-ethylhexyl, nonyl, decyl and dodecyl; and vinyl, allyl, propenyl, butenyl, octenyl, nonenyl, decenyl, dodecenyl, tetradecenyl, hexadecenyl and octadecenyl. M is selected from hydrogen, water-solubilizing cations such as potassium and sodium, and ammonium including aliphatic amines such as monoethanolamine, diethanolamine, triethanolamine and $C_1$-$C_4$ alkylamines such as methylamine, dimethylamine, ethylamine, diethylamine, methylethylamine, propylamine, methylpropylamine and methylbutylamine.

A beta-substituted acrylic acid or salt thereof to be used in this invention is prepared according to a method desctibed in R. Scheffold and P. Dabs, Helv. chim. Acta., 50, 798 (1967) or A. W. Noltes et al., Rec. Trav. Chim., 80, 1334 (1961).

The deodorizing agent of this invention can be used alone, or in mixtures of said agents, or in combination with other conventional deodorizing agents, sterilizing agents, surface active agents and the like.

The deodorizing agent of this invention is usually applied in the form of an aqueous solution or a water-alcohol solution. If it can not be dissolved completely in water or water-alcohol solution, the deodorizing agent can be used in the form of an emulsion, and no particular disadvantage is brought about if it is applied in the form of an emulsion. In some cases, it can be used in the form of powders or granules.

It is preferred that the deodorizing composition contains the effective ingredient of formula (I) or formula (II) or mixtures thereof in an amount of 0.1 to 5% by weight.

A smell removing and deodorizing composition in the form of a powder or granules, according to this invention, comprises 0.1 to 5 weight percent of said effective ingredient of formula (I) or formula (II) or mixtures thereof, up to 5 weight percent of other desired ingredients and the balance, to 100 weight percent, of an inorganic filler. As the filler, there can be used Glauber's salt (sodium sulfate), diatomaceous earth and sodium tripolyphosphate. To endow the composition with a detergent function, there can be incorporated therein from 1 to 5 weight percent of conventional anionic synthetic non-soap organic surfactants such as sodium alkylbenzene sulfonates in which the alkyl group has 8 to 18 carbon atoms, sodium alkyl (C8–C18) ether sulfates and sodium alpha-olefin (C13–C20) sulfonates. To improve the deodorizing effect, there can be further added thereto from 0.1 to 5 weight percent of citric acid, maleic acid, fumaric acid, or alkali metal, alkaline earth metal or ammonium salts of said acids. To endow the composition with sterilizing activity, there can be incorporated therein from 0.01 to 0.1 weight percent of a conventional sterilizing agent such as hexachlorophene, 3,4,4'-trichlorocarbanilide and 3-trichloromethyl-4,4'-dichlorocarbanilide.

A liquid composition according to this invention comprises 0.1 to 5 weight percent of said effective ingredient of formula (I) or formula (II) or mixtures thereof, up to 5 weight percent of other desired ingredients and the balance, to 100 weight percent, of a solvent. As the solvent, there are used water, a lower alkyl alcohol having one to three carbon atoms, acetone and mixtures thereof. To endow the liquid composition with detergent power, there are used from 1 to 5 weight percent of an anionic surfactant as mentioned above, or a water-soluble nonionic synthetic organic surfactant such as an adduct of polyalcohol or a higher alcohol and ethylene oxide, i.e. sorbitan fatty acid ester, polyoxyethylene lauryl ether. to provide the liquid composition with an augmented deodorizing effect, there are used from 1 to 5 weight percent of water-soluble aldehydes such as glyoxal and formaldehyde, water-soluble inorganic acids such as phosphoric acid and water-soluble organic acids such as malic acid and malonic acid. As the water-soluble sterilizer, there are used from 0.1 to 1 weight percent of benzalkonium chloride, benzethonium chloride and polyalkylamino ethylglycine. Moreover, when the effective ingredient is not soluble or when an oily substance such as liquid paraffin is incorporated into the composition, the composition can be used in the form of an emulsion. As the emulsifier, there can be used 1 to 5 weight percent of conventional emulsifying agents such as polyoxyethylene nonylphenyl ether wherein the number of oxyethylene units in the molecule is from 8 to 12.

This invention will now be described in more detail by reference to the following illustrative Examples.

EXAMPLE 1

An aqueous solution of 0.1 mole/liter of cystine, as a mercaptan substance, was reacted with 0.1 mole/liter of betaacetyl-acrylic acid, beta-methylbenzoyl-acrylic acid or beta-(nonylbenzoyl)-acrylic acid at room temperature (18°-25° C.), and the residual amount of cystine was measured at prescribed time intervals by the analytical method using potassium iodate. The excellent cystine removing effects shown in Table 1 were obtained. For comparison, the data obtained with a typical example of a conventional deodorizing agent, namely, lauryl methacrylate, are also shown in Table 1.

Table 1

| Active Ingredient | Residual Cystine content (%, based on original content) | | | |
|---|---|---|---|---|
| | Just After Reaction | After 0.5 Hour | After 1 Hour | After 3 Hours |
| beta-acetyl-acrylic acid | 3 | 1 | 0 | 0 |
| beta-methylbenzoyl-acrylic acid | 4 | 2 | 0 | 0 |
| beta-nonylbenzoyl-acrylic acid | 5 | 2 | 0 | 0 |
| lauryl methacrylate (comparison) | 94 | 90 | 88 | 86 |

From the results shown in the above Table, it will readily be understood that the compounds of this invention have an excellent activity for removing mercaptans.

EXAMPLE 2

A mixture composed of fish flesh and water was decomposed at 30° C. for 24 hours, and 10 g of the decomposed mixture, as a source of bad odor, was charged into a wide-mouth bottle having a capacity of 1 liter. Then, 1 milliliter of a 1% aqueous solution of beta-acetyl-acrylic acid was added dropwise to the contents of the bottle. The mercaptan, hydrogen sulfide and ammonia contents were determined at the prescribed time intervals. The excellent effects shown in Table 2 were obtained.

Table 2

| | Before Addition | After 1 Hour | After 2 Hours | After 3 Hours | After 5 Hours |
|---|---|---|---|---|---|
| Mercaptan Concentration (ppm) | 150 | 40 | 20 | 8 | 0 |
| Hydrogen Sulfide Concentration (ppm) | 45 | 5 | 0 | 0 | 0 |
| Ammonia Concentration (ppm) | 80 | 18 | 5 | 0 | 0 |

EXAMPLE 3

The same experiment as described in Example 2 was conducted similarly by using a 1% water-alcohol solution (water/alcohol=5/5) of beta-methylbenzoyl acrylic acid. The results obtained are shown in Table 3.

Table 3

| | Before Addition | After 1 Hour | After 2 Hours | After 3 Hours | After 5 Hours |
|---|---|---|---|---|---|
| Mercaptan Concentration (ppm) | 200 | 45 | 25 | 13 | 3 |
| Hydrogen Sulfide Concentration (ppm) | 50 | 10 | 0 | 0 | 0 |
| Ammonia Concentration (ppm) | 120 | 30 | 15 | 0 | 0 |

The embodiments of the invention in which an exclusive property or privilege is claimed are defined as follows:

1. A method for deodorizing odoriferous materials characterized by containing one or more of mercaptans, hydrogen sulfide, ammonia or amines as a bad-smelling component, which comprises applying to said material an effective deodorizing amount of a deodorizing compound or a mixture of deodorizing compounds selected from the group consisting of (A) a compound having the formula

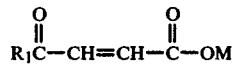

and (B) a compound having the formula

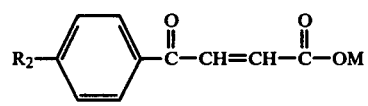

wherein M is hydrogen, sodium, potassium, ammonium, monoethanolamine, diethanolamine, triethanolamine, methylamine, dimethylamine, ethylamine, diethylamine, methylethylamine, propylamine, methylpropylamine or methylbutylamine, $R_1$ is alkyl having one to 20 carbon atoms or alkenyl having 2 to 20 carbon atoms, and $R_2$ is hydrogen, alkyl having one to 20 carbon atoms or alkenyl having two to 20 carbon atoms, sufficient to substantially reduce the content of said bad-smelling component of the odoriferous material.

2. The method according to claim 1, wherein said deodorizing compound is applied to the odoriferous material in the form of a solution or an emulsion in a liquid carrier selected from the group consisting of water, an alkanol having one to 3 carbon atoms, acetone and mixtures thereof, said solution or emulsion containing from 0.1 to 5 weight percent of said deodorizing compound.

3. The method according to claim 1, wherein said deodorizing compound is applied to the odoriferous material in the form of a powder or granules containing 0.1 to 5 weight percent of said deodorizing compound and the balance consists essentially of a filler.

4. The method of claim 1 wherein said compound is selected from the group consisting of beta-acetyl-acrylic acid, beta-methylbenzoyl-acrylic acid and beta-nonylbenzoyl-acrylic acid.

* * * * *